(12) United States Patent
Sun et al.

(10) Patent No.: US 10,302,484 B2
(45) Date of Patent: May 28, 2019

(54) OPTICAL SENSOR MODULE

(71) Applicant: Novatek Microelectronics Corp., Hsinchu (TW)

(72) Inventors: Cheng-Kuang Sun, Hsinchu (TW); Ying-Neng Huang, Taichung (TW)

(73) Assignee: Novatek Microelectronics Corp., Hsinchu (TW)

( * ) Notice: Subject to any disclaimer, the term of this patent is extended or adjusted under 35 U.S.C. 154(b) by 143 days.

(21) Appl. No.: 15/628,648

(22) Filed: Jun. 21, 2017

(65) Prior Publication Data
US 2018/0209844 A1   Jul. 26, 2018

Related U.S. Application Data

(60) Provisional application No. 62/450,049, filed on Jan. 24, 2017.

(51) Int. Cl.
| | |
|---|---|
| *H01L 27/00* | (2006.01) |
| *G01J 1/44* | (2006.01) |
| *H01L 31/16* | (2006.01) |
| *H01L 31/075* | (2012.01) |
| *G06K 9/00* | (2006.01) |

(52) U.S. Cl.
CPC .............. *G01J 1/44* (2013.01); *G06K 9/0004* (2013.01); *G06K 9/00013* (2013.01); *H01L 31/075* (2013.01); *H01L 31/162* (2013.01); *G01J 2001/446* (2013.01); *Y02E 10/50* (2013.01)

(58) Field of Classification Search
CPC ....... H01L 31/16; H01L 31/167; H01L 31/73; G06K 9/0004
USPC ................................ 250/208.1, 208.2, 214.1
See application file for complete search history.

(56) References Cited

U.S. PATENT DOCUMENTS

| | | | |
|---|---|---|---|
| 2005/0189624 A1* | 9/2005 | Sun ................... | H01L 27/14618 257/666 |
| 2013/0194199 A1 | 8/2013 | Lynch et al. | |
| 2014/0036168 A1 | 2/2014 | Ludwig | |
| 2018/0228414 A1* | 8/2018 | Shao .................. | A61B 5/14552 |

* cited by examiner

*Primary Examiner* — Kevin K Pyo
(74) *Attorney, Agent, or Firm* — JCIPRNET

(57) ABSTRACT

An optical sensor including a substrate and a plurality of pixel units are provided. The pixel units are disposed on the substrate, and each of the pixel units includes a light source element, a light sensor element, a circuit unit, and an isolation element. Herein, the light source element emits light, the light sensor element senses an optical image. The circuit unit is configured to drive the light source element to emit light and to drive the light sensor element to sense the optical image. The isolation element isolates the light sensor element from the light source element. In addition, the light source element is disposed between the isolation element of the respective pixel unit and an isolation element of a neighboring pixel unit.

16 Claims, 6 Drawing Sheets

OPTICAL SENSOR MODULE

CROSS-REFERENCE TO RELATED APPLICATION

This application claims the priority benefit of U.S. provisional application Ser. No. 62/450,049, filed on Jan. 24, 2017. The entirety of the above-mentioned patent application is hereby incorporated by reference herein and made a part of this specification.

BACKGROUND OF THE INVENTION

1. Field of the Invention

The invention relates to an optical sensor module, in particular, to an optical sensor module having advantages of uniform illuminating light, high fill factor, and high aperture ratio.

2. Description of Related Art

Recently, varieties of optical sensor modules are developed for applying to many products. The optical sensor module can be utilized for checking the health state, such as heart rate, blood pressure, etc., and exercise level of people and can also be used in electronic devices for detecting fingerprint.

FIG. 1 illustrates a structural cross-sectional view of a convention optical sensor module. In FIG. 1, a convention optical sensor module 100 includes a backlight element 101, a photodiode array 102, a readout circuit Tr, a light blocking or isolation element 103, and a cover lens 104. The optical sensor module 100 has a relatively large height due to the backlight element 101 disposed in the bottom of the optical sensor module 100. The light blocking or isolation element 103 is disposed between the backlight element 101 and the two photodiode array 102 and the readout circuit Tr to prevent the photodiode array 102 from directly detecting the light L1 emitted from the backlight element 101 that results in interference. The quality of a resultant image (e.g., fingerprint image) may be not good enough if the efficiency of using the light blocking or isolation element 103 is low.

FIG. 2 illustrates a structural cross-sectional view of another convention sensor module. Referring to FIG. 2, a convention optical sensor module 200 includes a side-emitting light source 201, a photo diode array 202, a readout circuit Tr, and a cover lens 203. The side-emitting light source 201 of the optical sensor module 200 is disposed in the lateral side of the cover lens 203, and the photodiode array 202 detects the light L2 reflected from the upper surface (i.e., the touched surface) of the cover lens 203, when an object (e.g., finger) touches the cover lens, by frustrated total internal reflection (FTIR). The height of the optical sensor module 200 may be lower than the height of the optical sensor module 100 in FIG. 1. However, the fingerprint image usually does not have a good uniformity due to the side-emitting light source 201.

SUMMARY OF THE INVENTION

Accordingly, the invention is directed to an optical sensor module having advantages of uniform illuminating light, high fill factor, and high aperture ratio.

The invention provides an optical sensor including a substrate and a plurality of pixel units. The pixel units are disposed on the substrate, and each of the pixel units includes a light source element, a light sensor element, a circuit unit, and an isolation element. Herein, the light source element emits light, the light sensor element senses an optical image. The circuit unit is configured to drive the light source element to emit light and to drive the light sensor element to sense the optical image. The isolation element isolates the light sensor element from the light source element. In addition, the light source element is disposed between the isolation element of the respective pixel unit and an isolation element of a neighboring pixel unit.

In one embodiment of the invention, the light sensor element is disposed under a space defined by the isolation element.

In one embodiment of the invention, the light source element and the isolation element are located in a first layer on the substrate.

In one embodiment of the invention, the light sensor element and the circuit unit are located in a second layer on the substrate, and the second layer is under the first layer.

In one embodiment of the invention, the normal projection of the light source element and the normal projection of the circuit unit projected on the substrate overlap with each other.

In one embodiment of the invention, the light sensor element includes a positive-intrinsic-negative photodiode horizontally integrated or vertically integrated.

In one embodiment of the invention, the light sensor element is disposed inside a space defined by the isolation element.

In one embodiment of the invention, the light source element, the light sensor element and the isolation element are located in a first layer on the substrate.

In one embodiment of the invention, the circuit unit is located in a second layer on the substrate, and the second layer is under the first layer.

In one embodiment of the invention, a normal projection of the light source element and a normal projection of the light sensor element projected on the substrate overlap with a normal projection of the circuit unit projected on the substrate.

In one embodiment of the invention, the light sensor element includes two electrodes horizontally disposed in the space and a photoconductive film formed in the space.

In one embodiment of the invention, the light sensor element includes a positive electrode and a negative electrode horizontally or vertically disposed in the space and a photoconductive film formed in the space.

In one embodiment of the invention, the optical sensor further includes a covering element disposed on the plurality of pixel units.

In one embodiment of the invention, the circuit unit includes a readout circuit and a driving circuit. The readout circuit is connected to a readout line and configured to drive the light sensor element to sense the optical image. The driving circuit is connected to the light source element and configured to drive the light source element to emit light.

In one embodiment of the invention, the driving circuit includes a row select transistor having a first end, a second end and a control end. The first end of the row select transistor is coupled to the light source element, the second end of the row select transistor is coupled to a system voltage, and the control end of the row select transistor receives a row select signal.

In one embodiment of the invention, the driving circuit further includes a feedback transistor having a first end, a second end and a control end. The first end of the feedback transistor is coupled to the second end of the row select transistor, the second end of the feedback transistor is coupled to the system voltage, and the control end of the feedback transistor is coupled to the readout line.

Based on the above, as described in the embodiments of the invention, since the self-illuminating material serves as the light source element, the optical path in the optical sensor module is simplified so as to the uniform of the illuminating light. In addition, because the circuit unit is placed under the light source element, the light sensor element is disposed on a sufficient area and the circuit unit is implemented in a larger space with more circuit complexity. Therefore, the fill factor of each pixel unit is significantly improved, and the aperture ratio/opening rate of each pixel unit is increased. Further, the light source element, which is the self-illuminating material, can perform the displaying function.

The abovementioned features and advantages of the invention will become more obvious and better understood with regard to the following description of the exemplary embodiments and accompanying drawings in the below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Figure 1:
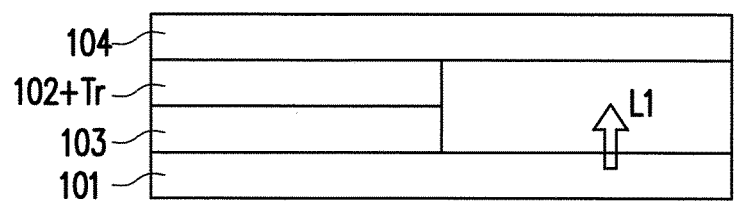
FIG. 1 illustrates a structural cross-sectional view of a convention optical sensor module.
Figure 2:
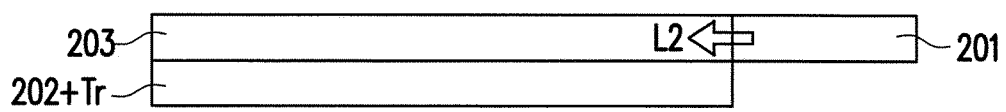
FIG. 2 illustrates a structural cross-sectional view of another convention optical sensor module.

In the following embodiments of the invention, a self-illuminating material, such as OLED (organic light emitting diode), is used as a light source element in an optical sensor module, and the self-illuminating light source element may be disposed in each pixel unit of the optical sensor module such that a uniform light source is provided. In such a way, a resultant image, e.g., fingerprint image, may have better uniformity than images generated by the conventional optical sensor modules using side-emitting light source or backlight source. In addition, the optical sensor modules according to the following embodiments may have a lower profile than the conventional optical sensor module of FIG. 1. In other words, the height of the optical sensor module in the invention is lower than the height of the conventional optical sensor module in FIG. 1.

Figure 3:
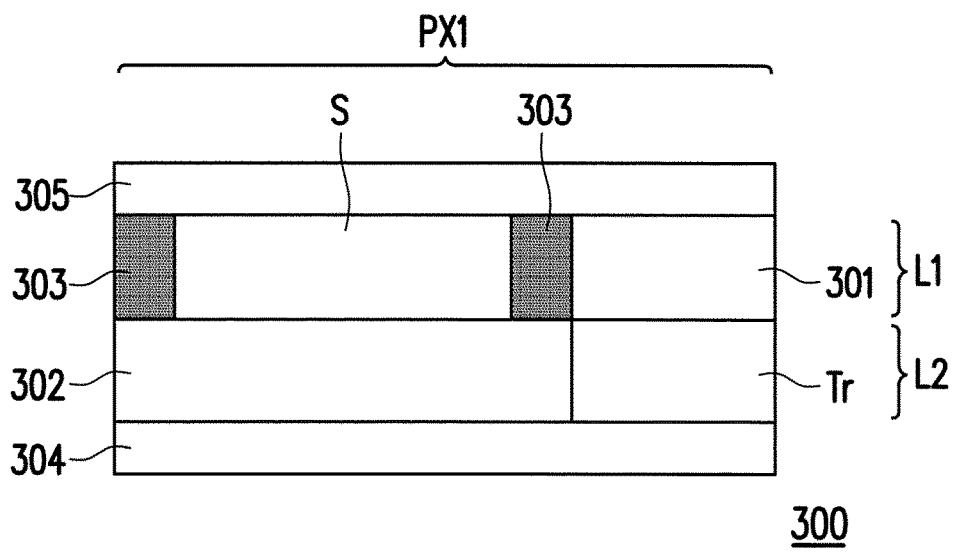
FIG. 3 illustrates a structural cross-sectional view of a pixel unit of an optical sensor module according to a first embodiment of the invention.

FIG. 3 illustrates a structural cross-sectional view of a pixel unit of an optical sensor module according to a first embodiment of the invention. Referring to FIG. 3, a pixel unit PX1 of an optical sensor module 300 is provided. The pixel unit PX1 includes a light source element 301, a light sensor element 302, a circuit unit Tr, and at least one isolation element 303. The pixel unit PX1 is disposed on a substrate 304 and covered by a cover lens 305 in the optical sensor module 300. Herein, the light source element 301 emits light, the light sensor element 302 senses an optical image, such as a fingerprint image, etc. The circuit unit Tr is configured to drive the light source element 301 to emit light and to drive the light sensor element 302 to sense the optical image. The isolation element 303 isolates the light sensor element 302 from the light source element 301.

In the present embodiment of FIG. 3, the light sensor element 302 may be a semiconductor device, such as photodiode, but the invention is not limited thereto. The circuit unit Tr includes a driving circuit and a readout circuit. The driving circuit drives the light source element 301 which is the self-illuminating light source element. The readout circuit is used for the light sensor element 302, such as photodiode(s), of the pixel unit PX1. In addition, the driving circuit and the readout circuit are disposed under the light source element 301, which is the self-illuminating light source (e.g., OLED). In such way, the light sensor element 302 of the pixel unit PX1 may be disposed on a sufficient area and the fill factor of each pixel unit may be significantly improved.

In FIG. 3, the symbol "Tr." denotes the circuit unit including the driving circuit for driving the light source element 301 (the self-illuminating light source element) and the readout circuit for the pixel unit PX1, which are fabricated in a thin film transistor (TFT) fabrication process (e.g., amorphous silicon (a-Si), Low Temperature Poly-silicon (LTPS), etc.). The readout circuit, which may be referred to FIG. 9, may include at least one transfer transistor (TX), a reset transistor (RST) and a row select transistor (RS1). The driving circuit is utilized for generating a driving current that drives the light source element 301 (the self-illuminating light source element) and may be implemented by various circuits. One of the embodiments of the driving circuit may be also referred to (but not limited to) FIG. 9, including a row select transistor (RS2) and a feedback transistor (FBT, which is optional). The isolation element 303 is required for stopping light from being directly received by light sensor element 302 without being reflected from the object (e.g., finger) touching the surface of the cover lens 305.

In the present embodiment, the light sensor element 302 is disposed under a space S defined by the isolation elements 303. In addition, the light source element 301 and the isolation elements 303 are located in a first layer L1 on the substrate 304. The light sensor element 302 and the circuit unit Tr are located in a second layer L2 on the substrate 304, and the second layer L2 is located under the first layer L1.

Additionally, in the present embodiment, the normal projection of the light source element 301 and the normal projection of the circuit unit Tr projected on the substrate 304 overlap with each other. However, the normal projections of the light source element 301 and the light sensor element 302 projected on the substrate 304 do not overlap with each other.

Figure 4:
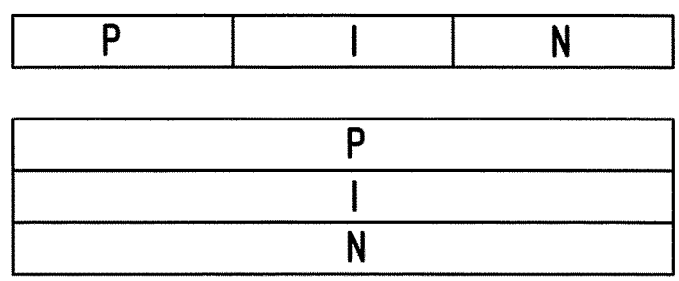
FIG. 4 illustrates two integrations of a Positive-Intrinsic-Negative photodiode.

In the first embodiment of FIG. 3, the light sensor element 302 may be a p-i-n (Positive-Intrinsic-Negative) photodiode fabricated by a TFT fabrication process such as a-si TFT process, and the p-i-n photodiode may be either horizontal integrated or vertical integrated as shown in FIG. 4.

Figure 5:
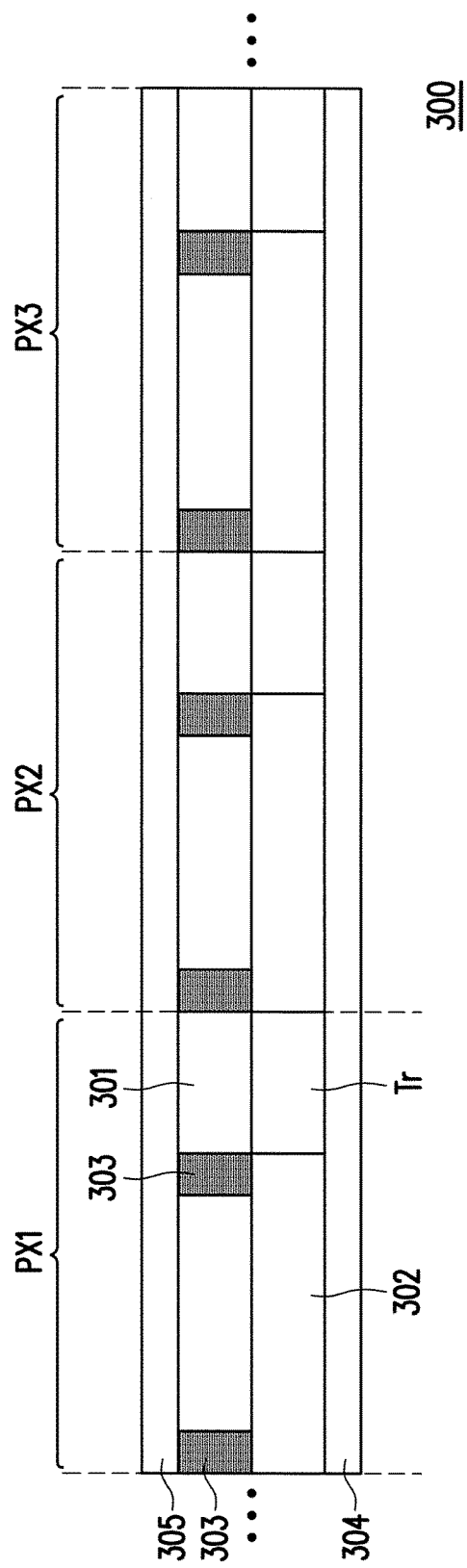
FIG. 5 illustrates a structural cross-sectional view of the optical sensor module according to the first embodiment.

Since the optical sensor module includes a plurality of pixel units arranged in an array, a structural cross-sectional view of the optical sensor module according to the first embodiment of FIG. 3 may look like FIG. 5. Referring to FIG. 5, the optical sensor 300 of the present embodiment includes the substrate 304 and a plurality of pixel units, such as pixel units PX1, PX2, PX3, etc., having the same structure. The pixel units are disposed on the substrate 304 and are covered by the cover lens 305. In addition, the light source element 301 is disposed between the isolation element 303 of the respective pixel unit PX1 and another isolation element 303 of the neighboring pixel unit PX2.

Figure 6:
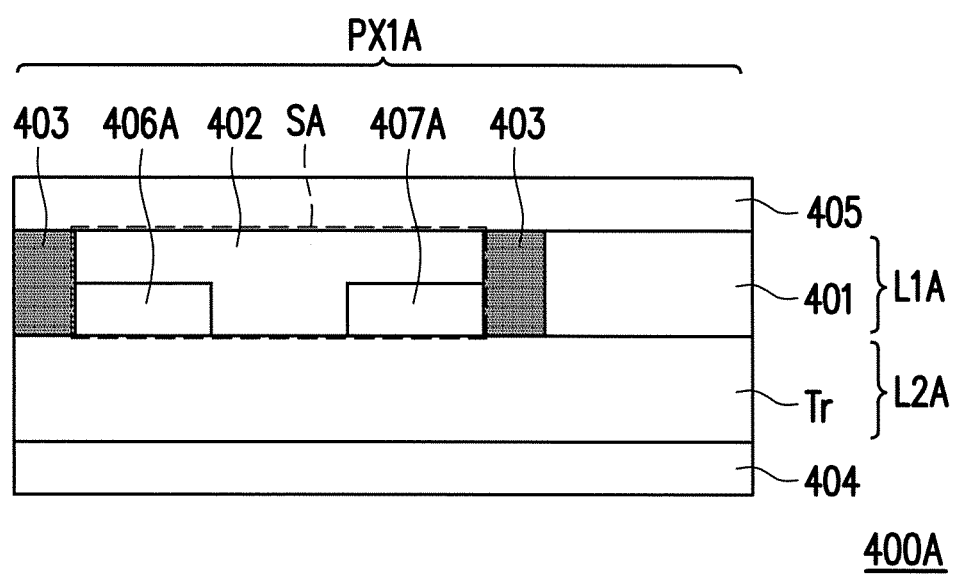
FIG. 6 illustrates a structural cross-sectional view of a pixel unit of an optical sensor module according to a second embodiment of the invention.

FIG. 6 illustrates a structural cross-sectional view of a pixel unit of an optical sensor module according to a second embodiment of the invention. Referring to FIG. 6, a pixel unit PX1A of an optical sensor module 400A is provided. The pixel unit PX1A includes a light source element 401, a light sensor element 402, a circuit unit Tr, and at least one isolation element 403. The pixel unit PX1A is disposed on a substrate 404 and covered by a cover lens 405 in the optical sensor module 400A. The functions of the light source element 401, the light sensor element 402, the circuit unit Tr, and the isolation element 403 of the present embodiment are similar to the functions of the light source element 301, the light sensor element 302, the circuit unit Tr, and the isolation element 303 of the first embodiment in FIG. 3 above. The differences between the present embodiment and the first embodiment in FIG. 3 are described hereinafter.

In the second embodiment in FIG. 6, the light sensor element 402 is disposed inside a space SA defined by the isolation elements 403 in the optical sensor module 400A. The light source element 401, the light sensor element 402 and the isolation element 403 are located in a first layer L1A on the substrate 404. The circuit unit Tr is located in a second layer L2A on the substrate 404, and the second layer L2A is located under the first layer L1A. In addition, the normal projection of the light source element 401 and the normal projection of the light sensor element 402 projected on the substrate 404 overlap with the normal projection of the circuit unit Tr projected on the substrate 404.

Furthermore, the light sensor element 402 in the second embodiment of FIG. 6 is fabricated in a different way from the light sensor element 302 in the second embodiment of FIG. 3.

To be more specific, the light sensor element 402 may be realized by an organic photoconductive film (OPF), which changes its electrical characteristics such as conductivity depending on the sensed light, coated in a region in which a positive electrode and a negative electrode are disposed. In FIG. 6, positive and negative electrodes 406A and 407A are horizontally disposed in the space SA, but the invention is not limited thereto. The electrodes 406A and 407A may be made of electrically conductive materials such as metal or transparent conductive material, e.g., Indium-Tin-Oxide (ITO). A voltage difference may be applied to the electrodes 406A and 407A, and a current is generated when the light sensor element 402 senses light. In other words, the light sensor element 402 includes two electrodes 406A and 407A horizontally disposed in the space SA and the light sensor element 402 further includes a photoconductive film formed in the space SA.

It should be noted here, from the plan view of the optical sensor 400A, each of the two electrodes 406A and 407A may include a plurality of parts. The parts of the electrode 406A and the parts of the electrode 407A are patterned to increase the area of one electrode facing the other one electrode, such as a fingers interlocked shape with intervals.

Figure 9:
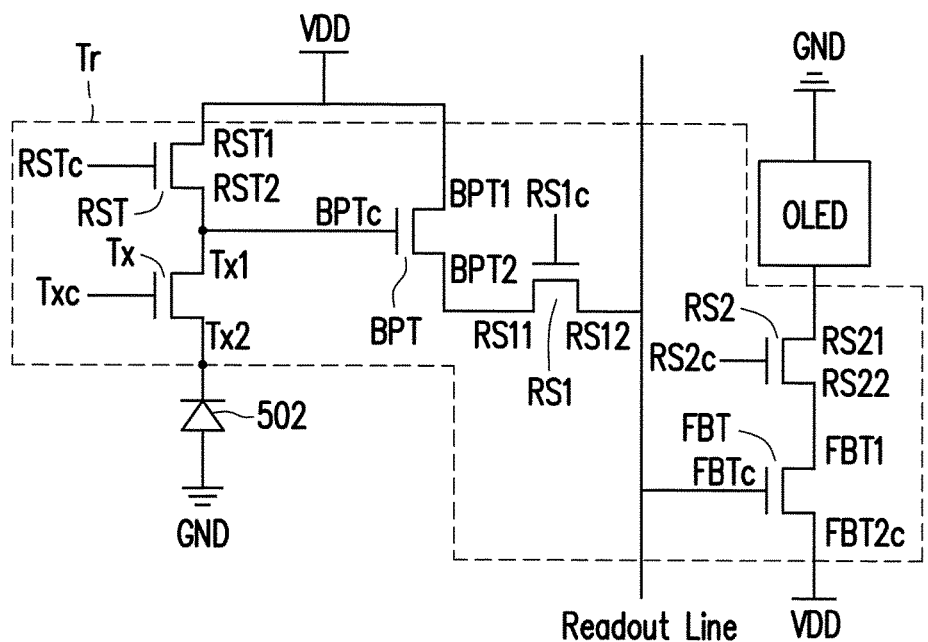
FIG. 9 is an exemplary schematic diagram of a circuit unit of a pixel unit of an optical sensor module of the invention.

In FIG. 6, "Tr." denotes the circuit including a driving circuit for driving the light source element 401 (the self-illuminating light source element) and a readout circuit for the pixel unit PX1A, wherein the driving circuit and the readout circuit may be referred to FIG. 9. The isolation element 403 is required for stopping light from being directly received by the light sensor element 402 without being reflected from the object (e.g., finger) touching the surface of the cover lens 405.

In the second embodiment of FIG. 6, the driving circuit and the readout circuit are disposed in the second layer L2A that is under the light source element 401 and also under the light sensor element 402. In such way, not only the light sensor element 402 of the pixel unit PX1A is disposed on a sufficient area but the readout circuit and the driving circuit may also be implemented in a larger space with more circuit complexity. Therefore, the fill factor of each pixel unit, such as pixel unit PX1A, may also be significantly improved.

Figure 7:
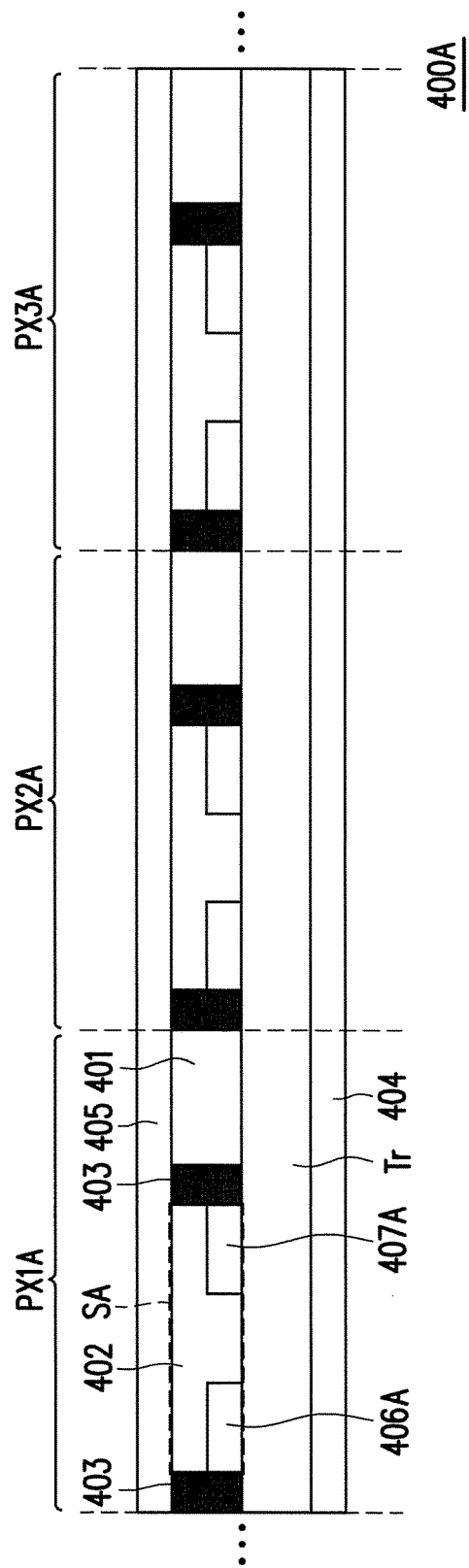
FIG. 7 illustrates a structural cross-sectional view of the optical sensor module according to the second embodiment of the invention.

Since the optical sensor module includes a plurality of pixel units arranged in an array, a structural cross-sectional view of the optical sensor module according to the second embodiment of FIG. 6 may look like FIG. 7. Referring to FIG. 7, the optical sensor 400A of the present embodiment includes the substrate 404 and a plurality of pixel units, such as pixel units PX1A, PX2A, PX3A, etc., having the same structure. The pixel units are disposed on the substrate 404 and are covered by the cover lens 405.

Figure 8:
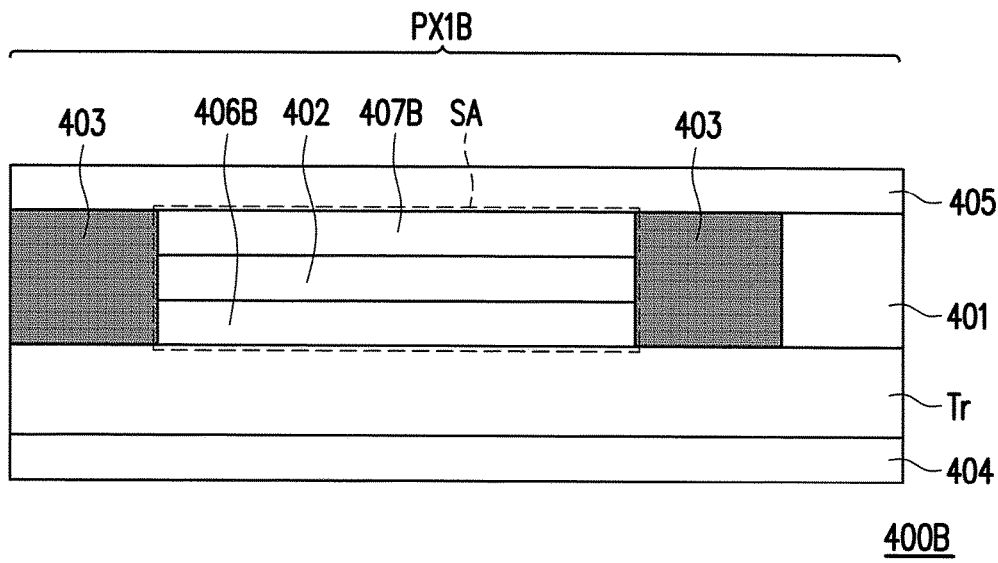
FIG. 8 illustrates a structural cross-sectional view of a pixel unit of an optical sensor module according to a third embodiment of the invention.

FIG. 8 illustrates a structural cross-sectional view of a pixel unit of an optical sensor module according to a third embodiment of the invention. Referring to FIG. 8, a pixel unit PX1B of an optical sensor module 400B is provided. The pixel unit PX1B is disposed on a substrate 404 and covered by a cover lens 405 in the optical sensor module 400B. The pixel unit PX1B includes a light source element 401, a light sensor element 402, a circuit unit Tr, and at least one isolation element 403. The difference between the third embodiment in FIG. 8 and the second embodiment in FIG. 6 is described as follows. The light sensor element 402 includes positive and negative electrodes 406B and electrode 407B vertically disposed in the space SA and a photoconductive film formed in the space SA and between the electrode 406B and electrode 407B. The electrode disposed above the other electrode (i.e. the electrode 407B disposed above the electrode 406B in FIG. 8) is a transparent electrode.

In other embodiments of the invention, the light sensor element may also include two electrodes vertically disposed and a photoconductive film disposed between the two electrodes. The lower one of the two electrodes and the photoconductive film are disposed inside the space defined by the isolation elements of a pixel unit, while the upper one of the two electrodes, different from the example shown in the FIG. 8, is disposed between the cover lens and the isolation elements of the pixel units of the optical sensor module 400B. The upper electrode may be continuously formed and shared by the pixel units of the optical sensor module 400B. The invention is not limited thereto.

FIG. 9 is an exemplary schematic diagram of a circuit unit of a pixel unit of an optical sensor module according to another embodiment of the invention. Referring to FIG. 9, a circuit unit Tr includes a readout circuit and a driving circuit. The readout circuit is connected to a readout line and configured to drive the light sensor element to sense the optical image. The driving circuit is connected to the light source element and configured to drive the light source element to emit light.

Additionally, the readout circuit includes a transfer transistor Tx, a reset transistor RST, a bypass transistor BPT, and a first row select transistor RS1. The transfer transistor Tx includes a first end Tx1, a second end Tx2 and a control end Txc, wherein the second end Tx2 of the transfer transistor Tx is coupled to a light sensor element 502, and the control end Txc of the transfer transistor Tx receives a transfer signal. The reset transistor RST includes a first end RST1, a second end RST2 and a control end RSTc, wherein the first end RST1 of the reset transistor RST is coupled to a system voltage VDD, the second end RST2 of the reset transistor RST is coupled to the first end Tx1 of the transfer transistor Tx, and the control end RSTc of the reset transistor RST receives a reset signal. The bypass transistor BPT includes a first end BPT1, a second end BPT2 and a control end BPTc, wherein the first end BPT1 of the bypass transistor BPT is coupled to the system voltage VDD, and the control end BPTc of the bypass transistor BPT is coupled to the first end Tx1 of the transfer transistor Tx. In addition, the first row select transistor RS1 includes a first end RS11, a second end RS12 and a control end RS1c, wherein the first end RS11 of the first row select transistor RS1 is coupled to the second end BPT2 of the bypass transistor BPT, the second end RS12 of the first row select transistor RS1 is coupled to the readout line, and the control end RS1c of the first row select transistor RS1 receives a first row select signal.

Moreover, the driving circuit includes a second row select transistor RS2 and a feedback transistor FBT. The second row select transistor RS2 includes a first end RS21, a second end RS22 and a control end RS2c, wherein the first end RS21 of the second row select transistor RS2 is coupled to a light source element (such as OLED), the second end RS22 of the second row select transistor RS2 is coupled to the system voltage, and the control end RS2c of the second row select transistor RS2 receives a second row select signal. Additionally, the feedback transistor FBT includes a first end FBT1, a second end FBT2 and a control end FBTc, wherein the first end FBT1 of the feedback transistor FBT is coupled to the second end RS22 of the second row select transistor RS2, the second end FBT2 of the feedback transistor FBT is coupled to the system voltage VDD, and the control end FBTc of the feedback transistor FBT is coupled to the readout line.

The driving circuit is utilized for generating a driving current that drives the light source element (the self-illuminating light source element) and may be implemented by various circuits.

In the present embodiment, the operation of the driving circuit driving the light source element (the self-illuminating light source, such as OLED) and the operation of the readout circuit for the light sensor element (such as photodiode) may be synchronized by using a control signal controlling both the first row select transistor RS1 and the second row select transistor RS2. In such way, the light sensor element of a pixel unit may only receive light originated from the light source element of the pixel unit and reflected from a touched surface when an object (e.g., finger) touches the surface of the cover lens of the optical sensor module, and the interference caused by unwanted light originated from the light source elements of neighboring pixel units may not happen.

The feedback transistor is an optional element and is utilized for controlling the driving current of the light source element according to a readout signal used as a feedback signal. If the light received by the light sensor element is not enough, the resulted readout signal may have a larger voltage and control the feedback transistor to generate a larger driving current to the light source element. Consequently, the light source element may generate a higher light intensity, and the intensity of the light received by the light sensor element may be increased so as to generate an image having a better contrast.

In another embodiment, the driving circuit driving the self-illuminating light source may be modulated with a short duty cycle such that the interference from the unwanted light in the surroundings may not greatly influence the readout signal.

In yet another embodiment, the light source element (e.g., OLED) of the optical sensor module may further realize image display function if the driving circuit can provide such a circuit complexity. In this case, the optical sensing function and the image display function are switchable, and the driving circuit may include two parts switchable, one for driving the self-illuminating light source to realize optical sensing and the other for driving the self-illuminating light source to display image data.

The optical sensor module according to the embodiment of the invention may be fabricated with an OLED display panel in a fabrication process, formed on the same substrate, and the optical sensor module may be regarded as a part of the OLED display panel. For example, if the optical sensor module is fabricated with an OLED display panel of a mobile phone or a tablet device, the optical sensor module may be formed in a lower area of the OLED display panel, apart from the display active area for displaying function. In another example, the optical sensor module may be fabricated with the entire display active area of an OLED display panel (that is, the OLED display panel also plays as a larger optical sensor module) as long as the display quality is acceptable.

Summarily, in the invention, since the self-illuminating material serves as the light source element, the optical path in the optical sensor module is simplified so as to the uniform of the illuminating light. In addition, because the circuit unit is placed under the light source element, the light sensor element is disposed on a sufficient area and the circuit unit is implemented in a larger space with more circuit complexity. Therefore, the fill factor of each pixel unit is significantly improved, and the aperture ratio/opening rate of each pixel unit is increased. Further, the light source element, which is the self-illuminating material, can perform the displaying function.

It will be apparent to those skilled in the art that various modifications and variations can be made to the structure of the invention without departing from the scope or spirit of the invention. In view of the foregoing, it is intended that the invention cover modifications and variations of this invention provided they fall within the scope of the following claims and their equivalents.

What is claimed is:
1. An optical sensor, comprising:
a substrate; and
a plurality of pixel units, disposed on the substrate, and each of the plurality of pixel units comprising:
a light source element, emitting light;
a light sensor element, sensing an optical image;
a circuit unit, configured to drive the light source element to emit light and to drive the light sensor element to sense the optical image; and
an isolation element, isolating the light sensor element from the light source element, wherein the light source element is disposed between the isolation element of the respective pixel unit and an isolation element of a neighboring pixel unit.

2. The optical sensor according to claim 1, wherein the light sensor element is disposed under a space defined by the isolation element.

3. The optical sensor according to claim 2, wherein the light source element and the isolation element are located in a first layer on the substrate.

4. The optical sensor according to claim 3, wherein the light sensor element and the circuit unit are located in a second layer on the substrate, and the second layer is under the first layer.

5. The optical sensor according to claim 2, wherein the normal projection of the light source element and the normal projection of the circuit unit projected on the substrate overlap with each other.

6. The optical sensor according to claim 1, wherein the light sensor element comprises a positive-intrinsic-negative photodiode horizontally integrated or vertically integrated.

7. The optical sensor according to claim 1, wherein the light sensor element is disposed inside a space defined by the isolation element.

8. The optical sensor according to claim 7, wherein the light source element, the light sensor element and the isolation element are located in a first layer on the substrate.

9. The optical sensor according to claim 8, wherein the circuit unit is located in a second layer on the substrate, and the second layer is under the first layer.

10. The optical sensor according to claim 7, wherein a normal projection of the light source element and a normal projection of the light sensor element projected on the substrate overlap with a normal projection of the circuit unit projected on the substrate.

11. The optical sensor according to claim 7, wherein the light sensor element comprises two electrodes horizontally disposed in the space and a photoconductive film formed in the space.

12. The optical sensor according to claim 7, wherein the light sensor element comprises a positive electrode and a negative electrode horizontally or vertically disposed in the space and a photoconductive film formed in the space.

13. The optical sensor according to claim 1, further comprising a covering element disposed on the plurality of pixel units.

14. The optical sensor according to claim 1, wherein the circuit unit comprises:
 a readout circuit connected to a readout line and configured to drive the light sensor element to sense the optical image; and
 a driving circuit connected to the light source element and configured to drive the light source element to emit light.

15. The optical sensor according to claim 14, wherein the driving circuit comprises:
 a row select transistor comprising a first end, a second end and a control end, wherein the first end of the row select transistor is coupled to the light source element, the second end of the row select transistor is coupled to a system voltage, and the control end of the row select transistor receives a row select signal.

16. The optical sensor according to claim 15, wherein the driving circuit further comprises:
 a feedback transistor comprising a first end, a second end and a control end, wherein the first end of the feedback transistor is coupled to the second end of the row select transistor, the second end of the feedback transistor is coupled to the system voltage, and the control end of the feedback transistor is coupled to the readout line.

* * * * *